US 7,551,784 B2

(12) United States Patent
Narasimhan et al.

(10) Patent No.: US 7,551,784 B2
(45) Date of Patent: Jun. 23, 2009

(54) CONTINUOUS INFERENCE FOR SEQUENCE DATA

(75) Inventors: Mukund Narasimhan, Bellevue, WA (US); Paul A. Viola, Kirkland, WA (US); Michael Shilman, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 21 days.

(21) Appl. No.: 11/421,585

(22) Filed: Jun. 1, 2006

(65) Prior Publication Data

US 2007/0282538 A1 Dec. 6, 2007

(51) Int. Cl.
G06K 9/00 (2006.01)
G06K 9/62 (2006.01)

(52) U.S. Cl. .................. 382/228; 382/181; 704/251

(58) Field of Classification Search .................. None
See application file for complete search history.

(56) References Cited

U.S. PATENT DOCUMENTS 6,128,606 A * 10/2000 Bengio et al. .................. 706/10
2002/0046022 A1 * 4/2002 Rose et al. .................. 704/231

OTHER PUBLICATIONS

By Hu et al (Modeling improvement of the continuous hidden markov model for speech recognition, Acoustics, Speech, and Signal Processing, 1992. ICASSP-92., 1992 IEEE International Conference on vol. 1, Mar. 23-26, 1992 pp. 373-376, Digital Object Identifier 10.1109/ICASSP.1992.225894).*
Zhang et al (Power aware processor scheduling under average delay constraints, Proceedings of the 11th IEEE Realtime and Embedded Technology and Application Symposium RTAS '05, 11 pages, Mar. 7-10, 2005).*
Dupont et al. (Pattern Recognition, vol. 38, p. 1349-1371, 2005).*
Fei et al. (Proceedings of the The IEEE Computer Society's 12th Annual International Symposium on Modeling, Analysis, and Simulation of Computer and Telecommunications Systems (MAS-COTS'04), p. 1-12, 2004).*
Aarino ( Speech recognition with Hidden Markov Models in Visual communication, Master of Science Thesis, University of Turkuu, p. 1-78, 1999).*

* cited by examiner

*Primary Examiner*—Marjorie Moran
*Assistant Examiner*—Karlheinz R Skowronek
(74) *Attorney, Agent, or Firm*—Turocy & Watson LLP (57) ABSTRACT

Dynamic inference is leveraged to provide online sequence data labeling. This provides real-time alternatives to current methods of inference for sequence data. Instances estimate an amount of uncertainty in a prediction of labels of sequence data and then dynamically predict a label when an uncertainty in the prediction is deemed acceptable. The techniques utilized to determine when the label can be generated are tunable and can be personalized for a given user and/or a system. Employed decoding techniques can be dynamically adjusted to tradeoff system resources for accuracy. This allows for fine tuning of a system based on available system resources. Instances also allow for online inference because the inference does not require knowledge of a complete set of sequence data.

8 Claims, 7 Drawing Sheets

CONTINUOUS INFERENCE FOR SEQUENCE DATA

BACKGROUND

Many problems in information extraction can be reduced to segmenting/labeling sequences, including part-of-speech tagging (in natural language applications), phoneme tagging (in speech applications), and sequence alignment (in bioinformatics applications). Hidden state Markov Models are widely used for solving such problems. A hidden state corresponds to a label for each observation in an input sequence, and the Markov assumption specifies that the state corresponding to time step (or location) n is independent of the state corresponding to time steps prior to n−2 given the state of time step n−1. Two such models are linear chain Hidden Markov Models (HMMs) and Conditional Random Fields (CRFs). Both models have been widely used for solving many problems dealing with semi-structured input sequences due to their simplicity and effectiveness.

Traditionally, the Viterbi algorithm is used for decoding such models. This algorithm requires computing a forward pass over the input sequence to compute probabilities/scores, followed by a reverse pass to compute the optimal state/label sequence. Therefore, all the data must be seen before any of the hidden states can be inferred, and hence it cannot be directly applied to real-time/reactive applications, or to applications where there are strong latency and/or memory constraints.

Thus, models and/or classifiers for labeling sequence data are typically based on local information (in which case they are fast, but not very accurate) or based on global information (in which case they are more accurate, but have higher latency/memory requirements). Consider, for example, a software application assistant which tries to determine user intent based on a sequence of user actions. One method guesses what the user is trying to do based on a current user action, while another method waits for the user to finish doing what they are trying to do, and then guesses the user's intention based on the entire sequence. This produces either fast, inaccurate results or slow, high-cost, accurate results that also require knowledge of a complete set of sequence data. Online applications such as those found on the Internet and/or intranets generally require fast and highly accurate results to entice users to use their services. When functions cannot provide these types of characteristics, they are often left out of applications to avoid user dissatisfaction, leaving the applications with less than desired functionality.

SUMMARY

Dynamic inference is leveraged to provide online sequence data labeling. This provides real-time alternatives to current methods of inference for sequence data. Instances estimate an amount of uncertainty in a prediction of labels of sequence data and then dynamically predict a label when an uncertainty in the prediction is deemed acceptable. The techniques utilized to determine when the label can be generated are tunable and can be personalized for a given user and/or a system and the like. Employed decoding algorithms can be dynamically adjusted to tradeoff system resources for accuracy. This allows for fine tuning of a system based on available system resources. This is especially beneficial for mobile devices that can have limited power resources. Instances also allow for online inference because the instances employ techniques that do not require knowledge of a complete set of sequence data. Thus, label predictions can be provided even before a complete set of data has been processed, saving valuable processing resources and time.

To the accomplishment of the foregoing and related ends, certain illustrative aspects of embodiments are described herein in connection with the following description and the annexed drawings. These aspects are indicative, however, of but a few of the various ways in which the principles of the subject matter may be employed, and the subject matter is intended to include all such aspects and their equivalents. Other advantages and novel features of the subject matter may become apparent from the following detailed description when considered in conjunction with the drawings.

DETAILED DESCRIPTION

The subject matter is now described with reference to the drawings, wherein like reference numerals are used to refer to like elements throughout. In the following description, for purposes of explanation, numerous specific details are set forth in order to provide a thorough understanding of the subject matter. It may be evident, however, that subject matter embodiments may be practiced without these specific details. In other instances, well-known structures and devices are shown in block diagram form in order to facilitate describing the embodiments.

As used in this application, the term "component" is intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a computer component. One or more components may reside within a process and/or thread of execution and a component may be localized on one computer and/or distributed between two or more computers.

As used herein, the term to "infer" or "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in construction of new events or actions from a set of observed events and/or stored event data, whether or not the events are correlated in close temporal proximity, and whether the events and data come from one or several event and data sources.

Instances of the subject matter herein provide alternatives to current techniques of inference for sequence data. These instances estimate the amount of uncertainty in a guess about labels of the sequence data and then dynamically guess whenever the uncertainty is deemed acceptable. The techniques employed to determine when the label can be generated are tunable and can be personalized for different styles (e.g., novice users might require more immediate feedback, while experienced users do not want to be frequently interrupted). Instances utilize decoding algorithms that can dynamically tradeoff latency/memory usage/CPU usage and the like for accuracy. Thus, for example, when running on mobile devices (such as cell-phones/PDAs and the like), the algorithm can continuously adjust the parameters so that the resource utilization is a function of, for example, the available battery life. A substantially similar technique can be utilized to run on a broad spectrum of devices. More powerful devices (devices with more memory) can run with a smaller "lambda," (i.e., tunable parameter) while less powerful devices can have a larger lambda. The lambda parameter can be learned and/or can be set based on a user to allow for personalization and/or set based on a system according to its timing constraints and/or resource availability.

Although the Viterbi algorithm is an efficient and optimal method for decoding linear-chain Markov Models, it requires that the entire input sequence must be observed before the optimization can complete, and, thus, it cannot be directly applied to online/interactive/streaming scenarios without incurring significant (possibly unbounded) latency. A widely used approach with Viterbi methods is to break the input stream into fixed-size windows and apply Viterbi to each window, where the window-size determines a trade-off between latency and accuracy. In sharp contrast to the fixed size window methods, instances disclosed herein dynamically compute a certainty measure on observed data that allows a trade-off of window size (i.e., latency/delay) for expected accuracy. This approach gives a substantial improvement in performance over choosing a fixed window.

Instances provided herein allow a system to intelligently wait until it has seen enough of an input of sequence data to generate labels with sufficient confidence (based on, for example, specified costs for false positives and false negatives). False positives and false negatives can have a real monetary cost. For example, in credit card fraud monitoring, observing additional transactions before declaring the credit card as stolen can cost the credit card agency money (for the fraudulent transactions), while false alarms can cause the users to be unnecessarily annoyed (which can cost the company money if the customer decides to cancel their card). There are many additional types of online and/or reactive systems such as human activity detection and patient monitoring and the like that can benefit from instances herein.

The need for labeling states without requiring the entire future is also acutely necessary in adaptive user interfaces. For example, in an interactive handwriting system, it is desirable to recognize the characters as they are sketched in order to present a user with constant feedback. In this case, waiting until the user inputs the entire document (or even the entire sentence) can result in delaying the feedback for an unreasonable amount of time. On the other hand, observing some (limited) amount of the future input can increase the accuracy (or increase the confidence in the state labels). Therefore, it is desirable to have algorithms that can trade off accuracy for latency. Instances herein provide techniques that can employ algorithms that reduce the latency between the time a decoder receives an observation corresponding to a particular time step and the time at which the decoder generates the label for the observation.

Figure 1:
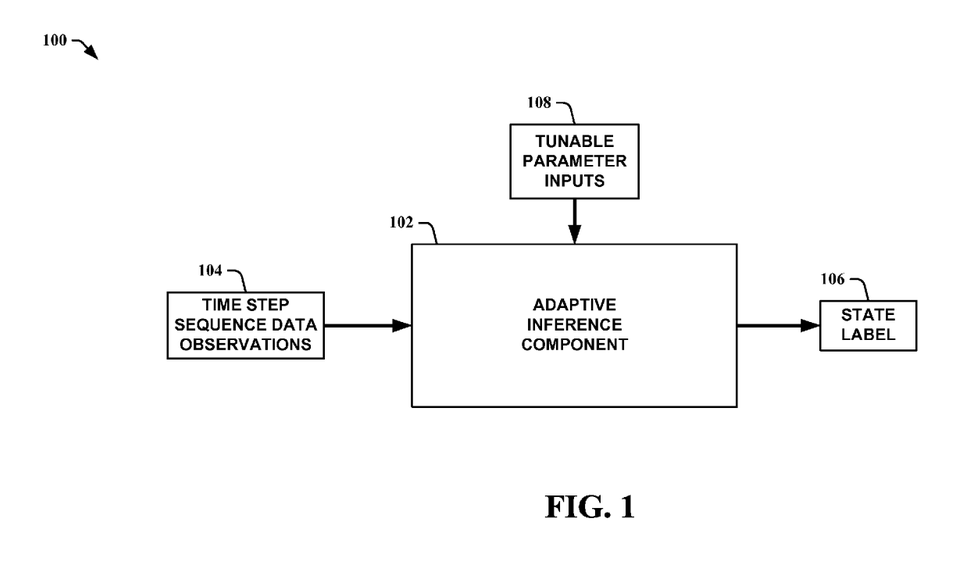
FIG. 1 is a block diagram of an adaptive inference system in accordance with an aspect of an embodiment.

In FIG. 1, a block diagram of an adaptive inference system 100 in accordance with an aspect of an embodiment is shown. The adaptive inference system 100 is comprised of an adaptive inference component 102 that receives time step sequence data observations 104 and provides a state label 106. The adaptive inference component 102 can also utilize tunable parameter inputs 108 to facilitate in dynamically determining a state label for a time step sequence data observation. The time step sequence data observations 104 can include, but are not limited to, data observations of any sequential data such as those extracted from speech, handwriting recognition, and/or bioinformatics (e.g., analyzing proteins—long chains) and the like. This includes very long sequences of data (even infinitely long sequences). The data comes in "elements" such as words of a document, codons (amino acids) of proteins (bioinformatics), and/or frames (segments of sound) of speech and the like. These elements are dynamically assigned a label by the adaptive inference component 102 and provided as the state label 106.

The adaptive inference component 102 leverages relationships between labels to facilitate in determining the state label 106 without requiring scanning of all sequence data. Explicitly modeling the dependencies between the labels yields a lower error rate. This allows the adaptive inference component 102 to provide the state label 106 online or in substantially real-time. Often an absolute certainty can be obtained that a present label will not change based on any additional future observations or a high certainty can be obtained that a present label will not change based on any additional future observations. The adaptive inference component 102 exploits these situations to allow the state label 106 to be provided substantially before all of a set of data has been reviewed. This saves, for example, vast system resources such as memory and/or computational resources over Naïve types of processes that require data to be stored in memory, maintained, and evaluated in case the last word changes the meaning.

Some applications require interactive participation and/or real-time processing such as, for example, speech—speech requires understanding of what is said before a speaker finishes—this is normally accomplished with a fixed window size (e.g., ten elements, output label, then 10 elements, output label—can lead to many errors). Instances provided herein permit the window size to dynamically change, allowing the determination of the appropriate window size to be done on-the-fly for a particular performance target. The particular performance target can be dynamic as well—such as, for example, with changing system resources such as battery life and the like.

Instances of the adaptive inference system 100 also allow computations to be accomplished more rapidly without introducing additional errors or with very few additional errors over an optimally determined solution (e.g., a solution without latency constraints). The adaptive inference system 100 employs algorithms that utilize an estimate of errors that would be made and as soon as the estimate of errors goes below a certain threshold it 100 stops and outputs the state label 106. Thus, the adaptive inference system 100 utilizes a "confidence dependent window-size."

There are two kinds of "dynamic"—data dependent dynamic and non-data dependent dynamic. Non-data dependent dynamic is conventional—e.g. can afford a window size of 10. The adaptive inference component 102 employs techniques that accounts for not making any more than X number of errors over the optimal answer and minimizes "correlated variables"—e.g., CPU usage related to an amount of battery power, etc. Thus, the adaptive inference component 102 can utilize small amounts of memory and can stop the algorithm and output a label at any time. In sharp contrast, traditional techniques must finish looking at all data before they can provide useful work. This allows the adaptive inference system 100 to drastically reduce the time it takes to provide the state label 106, substantially extending battery life of devices, substantially reducing CPU loading, and/or substantially reducing memory usage and the like.

The adaptive inference system 100 can also be employed in video applications, email applications, online web applications (e.g., the Internet and/or intranet applications), speech recognition applications, and/or mobile device applications (where system resources are crucial and ever changing) and the like. It 100 can be employed to facilitate in finding addresses to map, telephone numbers to lookup (e.g. put all these phone numbers in a phone book), and/or finding stock prices (e.g., taking stock ticker symbols and adding them to a portfolio) and the like. The adaptive inference system 100 can operate on data which is infinitely long (e.g., streaming data, etc.).

Figure 2:
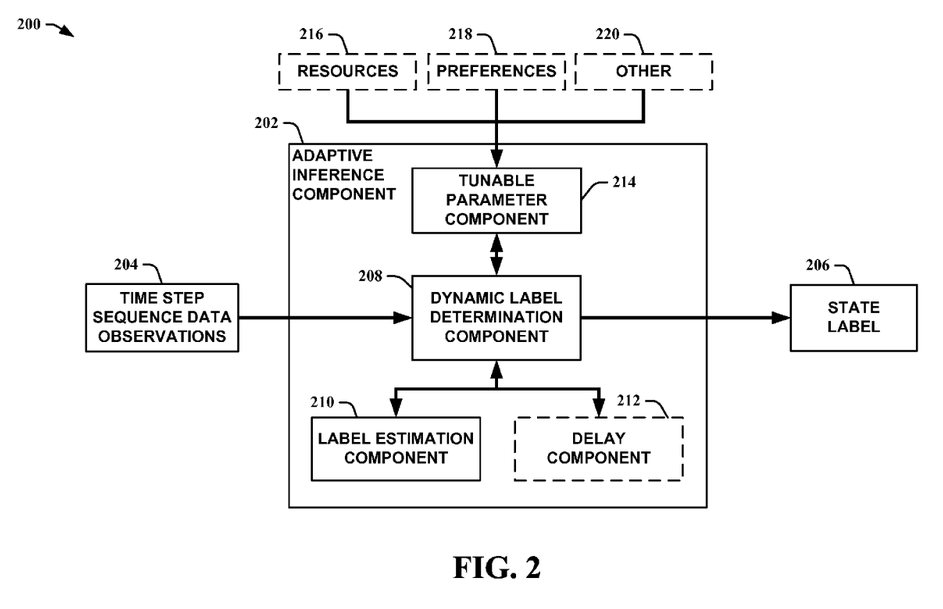
FIG. 2 is another block diagram of an adaptive inference system in accordance with an aspect of an embodiment.

Turning to FIG. 2, another block diagram of an adaptive inference system 200 in accordance with an aspect of an embodiment is illustrated. The adaptive inference system 200 is comprised of an adaptive inference component 202 that receives time step sequence data observations 204 and dynamically provides a state label 206. The adaptive inference component 202 is comprised of a dynamic label determination component 208, a label estimation component 210, an optional delay component 212, and a tunable parameter component 214. The tunable parameter component 214 can receive optional resources 216, optional preferences 218, and optional 'other' 220 to facilitate in tuning a parameter. The optional resources 216 can include system resources such as, for example, memory resources, CPU resources, and/or power resources (e.g., battery life) and the like. The optional preferences 218 can include user preferences and/or system preferences and the like. Optional other 220 represents other inputs such as, for example, hard overall constraints from a larger system that incorporates the adaptive inference system 200—such as, for example, time constraints based on a next step in processing that requires a certain amount of latency that impacts an amount of latency that the adaptive inference system 200 is allowed in which to perform its tasks.

In this instance, the dynamic label determination component 208 receives the time step sequence data observations 204. As noted supra, the time step sequence data observations 204 can come from a variety of types of data and can include, but is not limited to, infinite types of data streams as well. The dynamic label determination component 208 interacts with the tunable parameter component 214 to establish a threshold and/or delay requirements for label selections. The tunable parameter component 214 can utilize the optional inputs 216-220 to facilitate in dynamically tuning the parameter to compensate for changes in preferences and/or environment and the like.

The dynamic label determination component 208 takes a first observation and interacts with the label estimation component 210 to determine a label for the first observation and derive an estimation of an amount of uncertainty in that determination. Subsequent observations from the time step sequence data observations 204 are then employed by the label estimation component 210 to facilitate in evaluating if a correct label was chosen for the first observation. When the confidence in the selected label is within the threshold, the dynamic label determination component 208 outputs the label as the state label 206. In other instances, the optional delay component 212 is employed by the dynamic label determination component 208 to facilitate in bounding latency.

Thus, the dynamic label determination component 208 can utilize the optional delay component 212 to provide an absolute delay constraint (which can be influenced by the tunable parameter provided by the tunable parameter component 214) that forces a label selection based on the current label regardless of threshold requirements. It 208 can also utilize the optional delay component 212 to establish a trade-off or balance between delay and current estimation of label confidence. The trade-off or balance can be established by the tunable parameter which can also be influenced dynamically by available system resources and other changing constraints and the like. The optional delay component 212 is not necessary in instances where the adaptive inference system 200 is operating in a lossless mode. In other words, when an optimum answer from the adaptive inference system 200 is desired regardless of the amount of delay required to achieve that result. Despite not being bounded, instances provided herein still substantially outperform traditional techniques in lossless situations.

Figure 3:
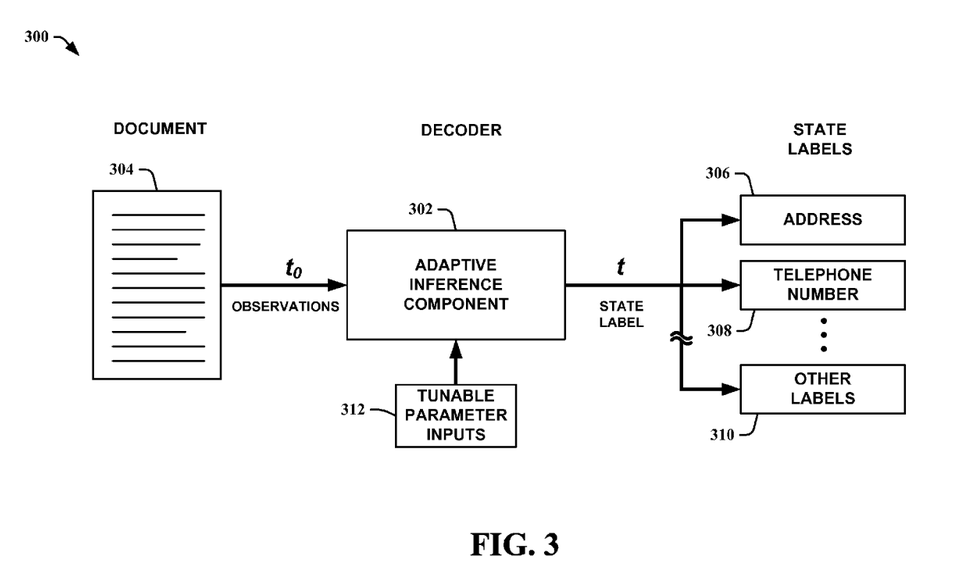
FIG. 3 is an example usage of an adaptive inference system in accordance with an aspect of an embodiment.

Looking at FIG. 3, an example usage of an adaptive inference system 300 in accordance with an aspect of an embodiment is depicted. The adaptive inference system 300 is employed as a decoder and is comprised of an adaptive inference component 302 that receives time step data observations from a document 304 with a first observation being received at time $t_0$. The elements, in this example, are words and/or phrasing from the document 304. The adaptive inference component 302 utilizes tunable parameter inputs 312 to facilitate in determining a high confidence label/delay trade-off for an observation. Once selected, a state label is provided as an output at time t. In this example, there is an "address" label output 306, a "telephone number" label output 308, and other labels output 310. The state labels 306-310 correspond to various observations received from the document 304. In this example, the adaptive inference system 300 can be employed to extract contact information from the document 304. The document 304 can be representative of a stand alone document and/or a web page and the like.

The adaptive inference component 302 employs algorithms provided herein that minimize the delay $(t-t_0)$, the latency between the receipt of the observation and when the state label is provided. Confidence in a label selection increases over subsequent observations, but this also increases system resource utilization and delay. Thus, instances provide a means to balance these factors while still providing a high confidence label. In some instances, delay can be guaranteed or bounded. This can be crucial for real-time and/or interactive applications where users may deem long delays unacceptable regardless of the confidence of the label.

Instances provided herein utilize techniques that respect the information present in state transitions and dynamically choose where to break the input stream based on a certainty measure such as, for example, the expected classification error rate. Infra, the two alternative approaches to traditional techniques are provided in detail and denoted as "Online Step" and "Online Variable Window," which leverage this insight in slightly different ways.

Online Step

The essence of the online step algorithm is that as it scans forward through the input sequence, the initial state becomes increasingly certain. At the same time, the latency, which is the average number of states that must be examined before the algorithm can output a single state, also increases. Once the certainty estimate reaches a dynamically-computed threshold in terms of the latency, this state is output and the next state in the sequence is estimated.

Assume that for each state r∈S, it can be determined (or at least estimated) that the probability that r is the state at time step $t_0$ on an optimal (Viterbi) path. In this case, it can be decided to generate a state for time step $t_0$ as long as there is only one state with sufficiently high probability (or equivalently if all the states but one have very low probability). In general, the exact probability that a given state is on the optimal path cannot be determined without all the observations. However, this probability can be estimated by using a limited number of future observations. Given some criteria for accuracy, it is possible in some cases to generate labels for past states well before the entire input is observed.

It should be noted that there can be a set of future observations for which some past state remains ambiguous. Hence, to get any guarantees on the performance of an online algorithm for this problem, some assumptions about the input are made.

Let $\tilde{P}(s,t_0|o_{0:T})$ be an estimate of the probability that state s is on the Viterbi path after observing the input up to time $T>t_0$. This probability can be computed as follows. Since the input up to time step $T>t_0$ has been observed, $P(a|o)$ can be computed, the probability of being at state a at time step T for each state a∈S. If state a is the state on the Viterbi path at time step T, then the state is $\overline{Prev}(t_0,a|o)$ at time step $t_0$. Therefore, the probability $\tilde{P}(s,t_0|o_{0:T})$ can be estimated by the following formula:

$$\sum_{s \in S_{\overline{Prev}_T}(t_0,s|o)=b} P_t(a \mid o) \quad \text{(Eq. 1)}$$

Observe that this is a distribution on the states at time $t_0$, based on observations up to and including $T>t_0$. Using this distribution, an estimate of the true distribution of the state s being on the Viterbi path at time step $t_0$ is utilized, several measures of how unreasonable it is to generate a state for time $t_0$ can be computed.

One simple measure is the expected classification error rate under this distribution—one minus the probability of the highest scoring state. In an interactive setting, where the user is presented with more than one option, an alternative measure can be the residual uncertainty in the state label, such as the entropy of the distribution. Observe that in the original scenario discussed, where state labels for a time step were generated when exactly one state in that time step was reachable, then essentially the side of the support of the distribution was utilized as the measure of how unreasonable it is to generate the state label. Let $M(t,t_0|o)$ denote the appropriate measure chosen. In these cases, a lower value indicates that the state can be generated with higher confidence, and a time $t>t_0$ is chosen so as to minimize this measure. On the other hand, it is desirable to minimize $t-t_0$, the number of additional observations needed before generating the state label. Combining these objectives, a time step t is sought so that $f(t)=M(t,t_0|o)+\lambda\cdot(t-t_0)$, where $M(t|o)$ is one of the measures described above. The parameter $\lambda$ is set based on the accuracy/latency trade off desired. Larger values of $\lambda$ penalize latency more and smaller values of $\lambda$ errors more. Therefore, for any fixed $\lambda>0$, an online algorithm is sought that finds a t that minimizes $M(t,t_0|o)+\lambda\cdot(t-t_0)$.

Clearly, if $M(t,t_0|o)$ can vary arbitrarily with t, then any deterministic (non-randomized) algorithm can do arbitrarily badly. Therefore, the following assumption is made on M: $M(t,t_0|o)$ is a decreasing function in t for any fixed $t_0$. Essentially, the more the future is observed, the more confidence is obtained about the present state. Under this assumption, the following online algorithm for optimizing $f(t)=M(t,t_0|o)+\lambda\cdot(t-t_0)$ is the best possible deterministic online algorithm: generate a label for time step $t_0$ whenever $M((t,t_0|o)<\lambda\cdot(t-t_0)$. Algorithms are judged in terms of their competitive ratio. An algorithm for optimizing f(t) is α-competitive if for every possible input (under the specified assumptions), the ratio of the solution produced by the algorithm to the optimal solution is no more than α (up to a constant). The following performance guarantee for the algorithm is obtained—the algorithm which generates a label for time step $t_0$ whenever $M(t,t_0|o)<\lambda\cdot(t-t_0)$ is 2-competitive under the assumption that $M(t,t_0|o)$ is a decreasing function in t for any fixed $t_0$.

Observe that since $M(t,t_0|o)$ is bounded from above, it will eventually generate a label for $t_0$ (no later than time step $$\frac{M(t_0, t_0 \mid o)}{\lambda}).$$

For example, if the expected classification error rate is used as the uncertainty measure, then 1 serves as an upper bound. If entropy is used, then $\log_2 S$ is an upper bound. As there is an upper bound on the latency, it is guaranteed that the algorithm will generate labels for all time steps.

Suppose the algorithm stops at time $T \geq t_0$. Clearly for all $t>T$, $f(t)>T$. For $t<T$, the least possible value of f(t) can happen if $M(t,t_0|o)=M(T,t_0|o)$, in which case this algorithm costs no more than twice the optimal. Since the algorithm stops if $M(T,t_0|o)<\lambda\cdot(T-t_0)$. Then for all $t>T$, the worst case occurs if $M(T+1,t_0|0)=0$, in which case:

$$f(T+1) = \lambda \cdot (T - t_0 + 1) > \lambda \cdot (T - t_0) \quad \text{(Eq. 2)}$$
$$= \frac{2 \cdot \lambda \cdot (T - t_0)}{2} > \frac{M(T, t_0 \mid o) + \lambda \cdot (T - t_0)}{2}$$
$$= \frac{f(T)}{2}$$

For all $t<T$, the worst case occurs if $M(T,t_0|o)=M(t_0,t_0|o)$ (so the observations between $t_0$ and T have provided no gain at all). In this case, the optimal solution is to pick $t=t_0$, and so the optimal value is $f(t_0)=M(T,t_0|o)$. Because the algorithm stops at time step T, and not before:

$$\lambda \cdot (T-t_0-1) \leq M(T,t_0|o)=M(t_0,t_0|o) \leq \lambda \cdot (T-t_0) \quad \text{(Eq. 3)}$$

Therefore, $$f(T) = M(T, t_0 \mid o) + \lambda \cdot (T - t_0) \quad \text{(Eq. 4)}$$
$$= M(T, t_0 \mid o) + \lambda \cdot (T - t_0 - 1) + \lambda \leq$$
$$2 \cdot M(T, t_0 \mid o) + \lambda \leq 2f(t_0) + \lambda$$

Thus, the algorithm picks a time which costs no more than 2 times the cost of any other time (up to a constant), and hence it is guaranteed to be 2-competitive.

Online Variable Window

The online variable window algorithm is similar to the online step algorithm above, only rather than computing the certainty of a single state, it estimates the certainty corresponding to an entire time window of states. Once the certainty of that window surpasses a threshold with respect to the length of the window, the entire window is output and the process begins again.

As before, the optimal break points cannot be determined with absolute certainty unless the entire input is read. In fact, any online algorithm can be made to behave arbitrarily badly by choosing the appropriate observation sequence. Therefore, modest assumptions are made about the input sequence, and under these assumptions, the optimal online algorithm is determined.

First, begin by quantifying the "loss" in labeling accuracy using a smaller window instead of the entire observation sequence. Suppose the Viterbi algorithm is run on observations from time step $t_0$ to time step T, and let $s_{early}^{(T)}$ be the state for time step T based on the observations up to time step T, and $s_{opt}^{(T)}$ be the optimal state based on the entire input observation. $s_{opt}^{(T)}$ may not be able to be computed because the input sequence can extend into the infinite future. To overcome this, $P_T(s|o)$ is used as an estimate for the probability that s is the state at time t on the optimal Viterbi path. Let a,b∈S be two potential states that can be generated at time step T. If state a is chosen for time step T, then the state for time step T−1 is $Prev_T(a)$, and the state for time step T−2 is $Prev_{T-1}(Prev_T(a))=Prev_T^2(a)$ and so on. Therefore, the difference in the states in the sequence caused by choosing a instead of b is:

$$Loss_T(a, b \mid o) = \sum_{k=0}^{T-t_0} 1_{\{Prev_T^k(a) \neq Prev_T^k(b)\}} \quad \text{(Eq. 5)}$$

This loss function can be efficiently computed by this simple recurrence relation:

$$LOSS_T(a,b|o)=1_{a \neq b}+LOSS_{T-1}(Prev_T(a|o),Prev_T(b|o),o) \quad \text{(Eq. 6)}$$

Therefore, the expected loss of picking the state a at time step T is:

$$Loss_T(a \mid o) = \sum_{b \neq a} P_T(b \mid o) \cdot Loss_T(a, b) \quad \text{(Eq. 7)}$$

This measures the expected number of incorrectly generated states by the choice of a at time step T. According to this loss function, the choice of state $s_{early}^{(T)}$ at time T that leads optimal loss for this window is given by:

$$s_{early}^{(T)} = \arg\min_{a \in S} Loss(a \mid o) \quad \text{(Eq. 8)}$$

Observe that this is a measure of loss for using the window $[t_0,T]$. As before, it is desirable to choose a window $[t_0,T]$ that minimizes $LOSS_T+\lambda(T-t_0)$, which can be done using the same algorithm.

Thus, instances herein provide effective techniques for low-latency optimal decoding of sequential input streams. Both the Online Variable Window algorithm and the Online Step algorithm achieve substantially higher performance than traditional techniques. Using these algorithms, instances can achieve virtually the same accuracy as the Viterbi algorithm, while using only a constant (small) amount of space, regardless of the length of the input.

In view of the exemplary systems shown and described above, methodologies that may be implemented in accordance with the embodiments will be better appreciated with reference to the flow charts of FIGS. 4-7. While, for purposes of simplicity of explanation, the methodologies are shown and described as a series of blocks, it is to be understood and appreciated that the embodiments are not limited by the order of the blocks, as some blocks may, in accordance with an embodiment, occur in different orders and/or concurrently with other blocks from that shown and described herein. Moreover, not all illustrated blocks may be required to implement the methodologies in accordance with the embodiments.

The embodiments may be described in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired in various instances of the embodiments.

Figure 4:
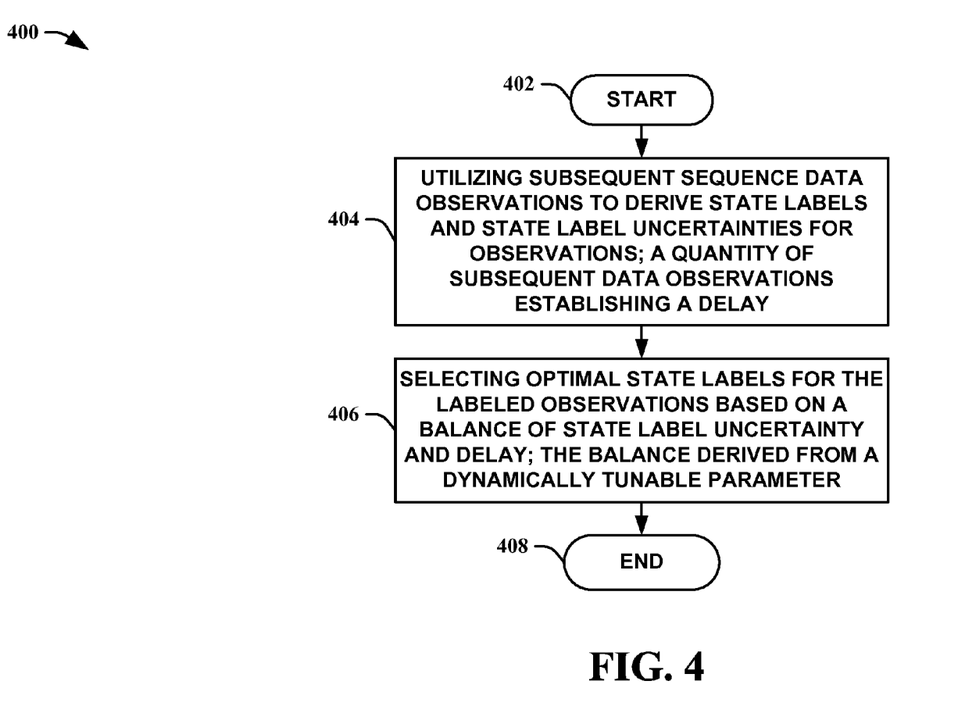
FIG. 4 is a flow diagram of a method of providing continuous inference for sequence data in accordance with an aspect of an embodiment.

Looking at FIG. 4, a flow diagram of a method 400 of providing continuous inference for sequence data in accordance with an aspect of an embodiment is shown. The method 400 starts 402 by utilizing subsequent sequence data observations to derive state labels and state label uncertainties for observations; a quantity of subsequent data observations establishing a delay 404. A state is assumed for a time step associated with an observation. There will be a degree of uncertainty regarding the assumed state that can be reduced by looking forward at future observations. The number or quantity of future observations relates to an amount of delay in processing labels. The more observations considered, the longer the delay.

Optimal state labels for the labeled observations are then selected based on a balance of state label uncertainty and delay; the balance derived from a dynamically tunable parameter 406, ending the flow 408. To operate within applications that run real-time and/or provide interactive participation, trade-offs between accuracy and latency typically occur. The dynamically tunable parameter allows the balance or tradeoff of these two changes based on environment (external influences) and/or preferences and the like. Thus, the tunable parameter can be tied to system resources, such as available battery power in a mobile device and the like, to dynamically alter the balance or tradeoff to compensate for reduced power and/or other computational resources.

Figure 5:
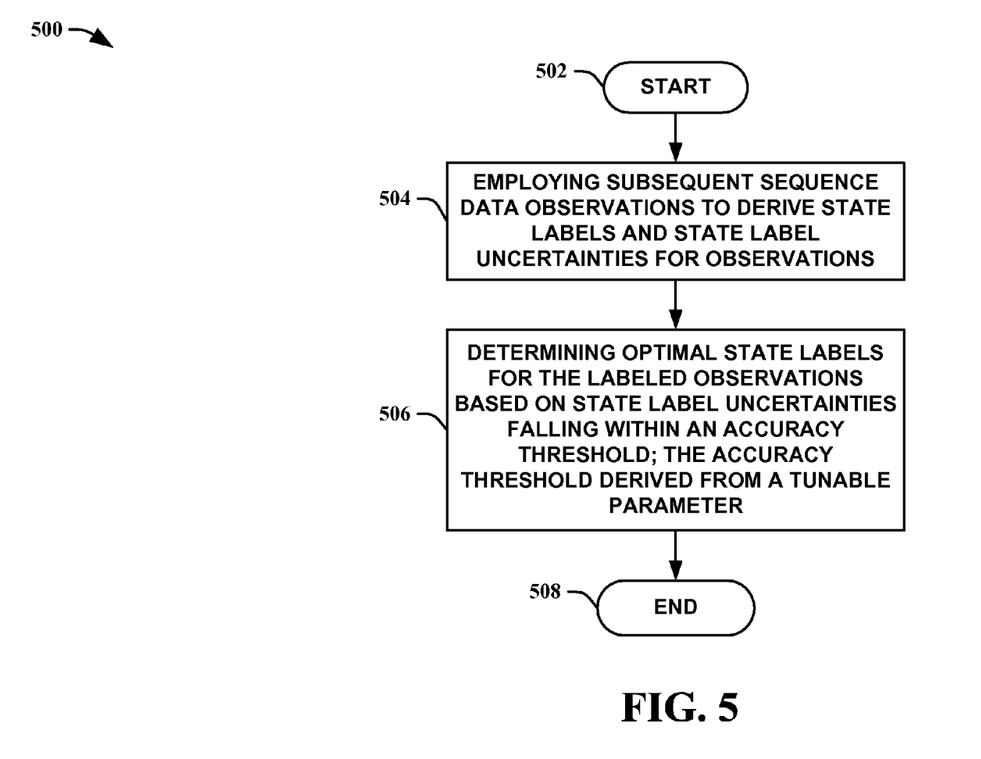
FIG. 5 is a flow diagram of a method of providing lossless inference for sequence data in accordance with an aspect of an embodiment.

Referring to FIG. 5, a flow diagram of a method 500 of providing lossless inference for sequence data in accordance with an aspect of an embodiment is depicted. The method 500 starts 502 by employing subsequent sequence data observations to derive state labels and state label uncertainties for observations 504. Optimal state labels for the labeled observations are then determined based on state label uncertainties falling within an accuracy threshold; the accuracy threshold derived from a tunable parameter 506, ending the flow 508. Some instances operate in a lossless fashion and are not limited by system resources and/or latency and the like. In these situations, accuracy is given the highest priority. However, even without latency bounds, instances provided herein can still substantially outperform traditional techniques for finding an optimum solution.

Figure 6:
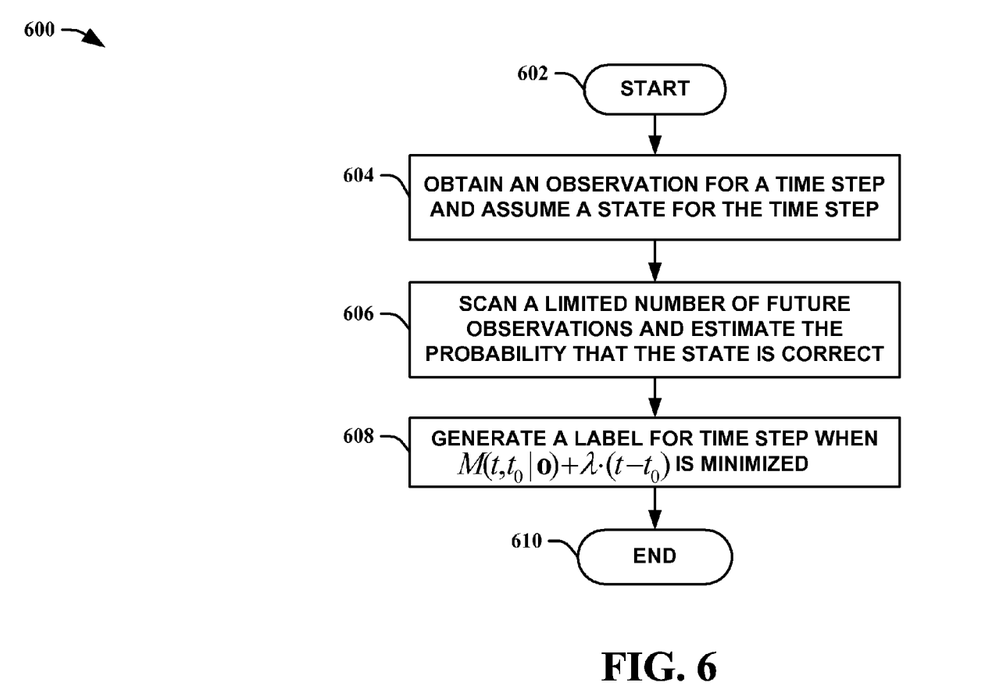
FIG. 6 is a flow diagram of a method utilizing an online step process in accordance with an aspect of an embodiment.

Turning to FIG. 6, a flow diagram of a method 600 utilizing an online step process in accordance with an aspect of an embodiment is illustrated. The method 600 starts 602 by obtaining an observation for a time step and assuming a state for the time step 604. An initial assumption is made so that initial estimations on certainty can be formed. A limited number of future observations are scanned and the probability that the state is correct is estimated 606. The number of scanned future observations is dependent on the following threshold being met. A label for the time step is generated when $M(t,t_0|o)+\lambda \cdot (t-t_0)$ is minimized 608, ending the flow 610. Thus, the state label is based on finding a time step t that minimizes $M(t,t_0|o)+\lambda \cdot (t-t_0)$ for any fixed tunable parameter $\lambda > 0$, where $M(t,t_0|o)$ is an appropriate measure.

Figure 7:
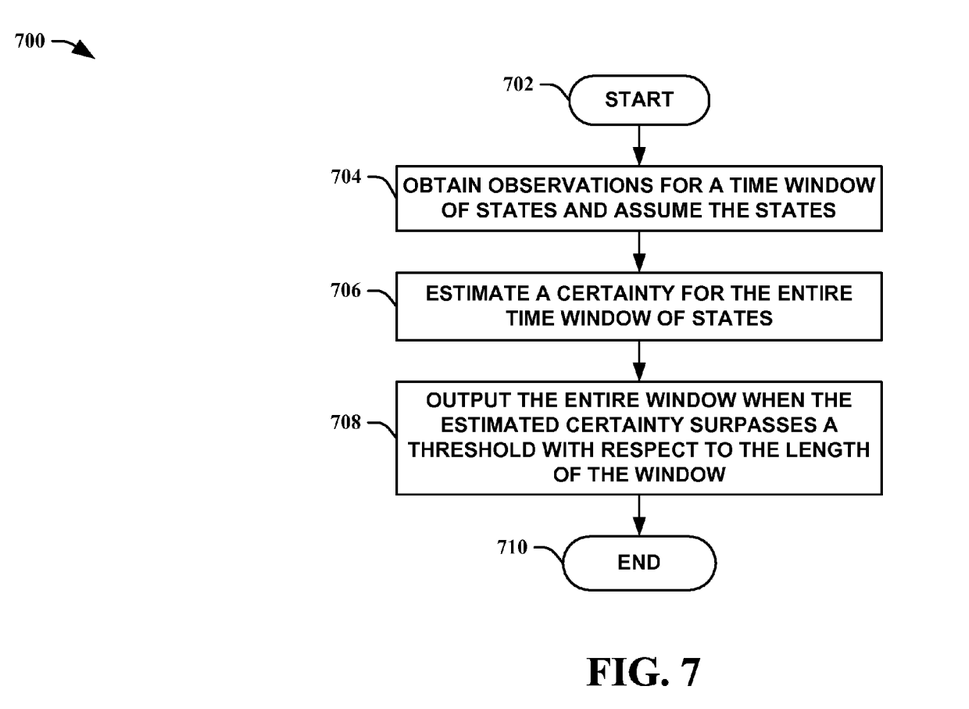
FIG. 7 is a flow diagram of a method utilizing an online variable window process in accordance with an aspect of an embodiment.

Looking at FIG. 7, a flow diagram of a method 700 utilizing an online variable window process in accordance with an aspect of an embodiment is shown. The method 700 starts 702 by obtaining observations for a time window of states and assuming the states 704. The assumption of the states enables an initial certainty to be established. A certainty for the entire time window of states is then estimated 706. This differs from the online step method which estimates a certainty for individual states. The entire window is output when the estimated certainty surpasses a threshold with respect to the length of the window 708, ending the flow 710. The threshold itself can be dynamic as can be the length of the window.

It is to be appreciated that the systems and/or methods of the embodiments can be utilized in continuous inference facilitating computer components and non-computer related components alike. Further, those skilled in the art will recognize that the systems and/or methods of the embodiments are employable in a vast array of electronic related technologies, including, but not limited to, computers, servers and/or hand-held electronic devices, and the like.

What has been described above includes examples of the embodiments. It is, of course, not possible to describe every conceivable combination of components or methodologies for purposes of describing the embodiments, but one of ordinary skill in the art may recognize that many further combinations and permutations of the embodiments are possible. Accordingly, the subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for providing continuous inference for sequence data, comprising a processor, wherein the processor comprises the following executable instructions:
   an estimation component that estimates an amount of uncertainty in a prediction of a label for a sequence data observation, the estimation component utilizes subsequent sequence data observations to re-evaluate the amount of uncertainty as each observation is received;
   a delay component that monitors an amount of delay since receiving an initial sequence data observation; and
   a determination component that employs an algorithm that dynamically selects and outputs a label for the sequence data observations when the amount of uncertainty and the amount of delay is within a threshold, the threshold determined by finding an output time t that minimizes the function $M(t,t_0|o)+\lambda \cdot (t-t_0)$, where $t_0$ is the time of a first sequence data observation, $M(t,t_0|o)$ is a measure of residual uncertainty in the label at time step $t_0$ given observations o, and $\lambda$ is a tunable parameter that indicates a preferred balance between label output delay and label confidence.

2. The system of claim 1 further comprising:
   a parameter component that determines the tunable parameter based on at least one of a user preference or available system resources.

3. The system of claim 2, the available system resources including one or more of battery power, memory, or processor.

4. The system of claim 1, the determination component yields to an absolute delay constraint that forces a label selection regardless of the threshold after an amount of delay equal to the delay constraint has elapsed.

5. The system of claim 4, the absolute delay constraint is based on the tunable parameter.

6. The system of claim 1, the determination component selects the label using the tunable parameter based on a tradeoff between accuracy and at least one of the amount of delay, memory usage, or processing usage.

7. The system of claim 1, the tunable parameter is influenced by accuracy constraints from one or more system resources.

8. The system of claim 7, the tunable parameter continuously adjusts accuracy constraints based on available battery power of a mobile device.

* * * * *